US00PP26417P2

(12) United States Plant Patent
Oostveen

(10) Patent No.: US PP26,417 P2
(45) Date of Patent: Feb. 16, 2016

(54) ***HIBISCUS* PLANT NAMED 'EXTRMAG'**

(50) Latin Name: *Hibiscus moscheutos*
Varietal Denomination: Extrmag

(71) Applicant: Cornelis A. Oostveen, De Kwakel (NL)

(72) Inventor: Cornelis A. Oostveen, De Kwakel (NL)

(73) Assignee: De Zonnebloem Breeding B.V., De Kwakel (NL)

( * ) Notice: Subject to any disclaimer, the term of this patent is extended or adjusted under 35 U.S.C. 154(b) by 225 days.

(21) Appl. No.: 13/998,609

(22) Filed: Nov. 15, 2013

(51) Int. Cl.
*A01H 5/02* (2006.01)

(52) U.S. Cl.
USPC ..... Plt./257

(58) Field of Classification Search
USPC ..... Plt./257
See application file for complete search history.

(56) References Cited

PUBLICATIONS

Plant Breeders' Right Plant Variety Database (PLUTO), QZ PBR 40852, publication date Dec. 15, 2013.*

* cited by examiner

*Primary Examiner* — Anne Grunberg
(74) *Attorney, Agent, or Firm* — C. A. Whealy

(57) ABSTRACT

A new and distinct cultivar of *Hibiscus* plant named 'Extrmag', characterized by its upright and somewhat outwardly spreading plant form; freely branching habit; freely flowering habit; large magenta-colored flowers; and good flower longevity.

2 Drawing Sheets

Botanical designation: *Hibiscus moscheutos.*
Cultivar denomination: 'EXTRMAG'.

BACKGROUND OF THE INVENTION

The present invention relates to a new and distinct cultivar of *Hibiscus* plant, botanically known as *Hibiscus moscheutos* and hereinafter referred to by the name 'Extrmag'.

The new *Hibiscus* plant is a product of a planned breeding program conducted by the Inventor in De Kwakel, The Netherlands. The objective of the breeding program is to create new *Hibiscus* plants with large attractive flowers.

The new *Hibiscus* plant originated from a cross-pollination in August, 2011 in De Kwakel, The Netherlands of a proprietary selection of *Hibiscus moscheutos* identified as code number CB11023, not patented, as the female, or seed, parent with a proprietary selection of *Hibiscus moscheutos* identified as code number CB11046, not patented, as the male, or pollen, parent. The new *Hibiscus* plant was discovered and selected by the Inventor as a single flowering plant from within the progeny of the stated cross-pollination in a controlled greenhouse environment in De Kwakel, The Netherlands in August, 2012.

Asexual reproduction of the new *Hibiscus* plant by vegetative cuttings in a controlled greenhouse environment in De Kwakel, The Netherlands since September, 2012 has shown that the unique features of this new *Hibiscus* plant are stable and reproduced true to type in successive generations.

SUMMARY OF THE INVENTION

Plants of the new *Hibiscus* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Extrmag'. These characteristics in combination distinguish 'Extrmag' as a new and distinct *Hibiscus* plant:

1. Upright and somewhat outwardly spreading plant form.
2. Freely branching habit.
3. Freely flowering habit.
4. Large magenta-colored flowers.
5. Good flower longevity.

Plants of the new *Hibiscus* can be compared to plants of the female parent selection. Plants of the new *Hibiscus* differ primarily from plants of the female parent selection in the following characteristics:

1. Plants of the new *Hibiscus* are more freely branching than plants of the female parent selection.
2. Plants of the new *Hibiscus* and the female parent selection differ in flower color as plants of the female parent selection have red-colored flowers.

Plants of the new *Hibiscus* can be compared to plants of the male parent selection. Plants of the new *Hibiscus* differ primarily from plants of the male parent selection in the following characteristics:

1. Plants of the new *Hibiscus* have darker green-colored leaves than plants of the male parent selection.
2. Plants of the new *Hibiscus* and the male parent selection differ in flower color as plants of the male parent selection have pink-colored flowers.

Plants of the new *Hibiscus* can be compared to plants of *Hibiscus moscheutos* 'Extrepink', disclosed in U.S. Plant Pat. No. 23,130. In side-by-side comparisons conducted in De Kwakel, The Netherlands, plants of the new *Hibiscus* differed primarily from plants of 'Extrepink' in the following characteristics:

1. Plants of the new *Hibiscus* were more freely branching than and not as vigorous as plants of 'Extrepink'.

2. Plants of the new *Hibiscus* had darker green-colored leaves than plants of 'Extrepink'.
3. Plants of the new *Hibiscus* and 'Extrepink' differed in flower color as plants of 'Extrepink' had light red purple-colored flowers with darker red purple-colored centers and venation.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of a typical flowering plant of 'Extrmag' grown in a container.

The photograph on the second sheet is a close-up view of a typical flower of 'Extrmag'.

DETAILED BOTANICAL DESCRIPTION

The aforementioned photographs and following observations, measurements and values describe plants grown during the late summer in five-liter containers in a glass-covered greenhouse in De Kwakel, The Netherlands and under cultural practices typical of commercial *Hibiscus* production. During the production of the plants, day temperatures ranged from 18° C. to 33° C. and night temperatures ranged from 18° C. to 25° C. Plants were 14 weeks old when the photographs and the description were taken. In the following description, color references are made to The Royal Horticultural Society Colour Chart, 2007 Edition, except where general terms of ordinary dictionary significance are used.

Botanical classification: *Hibiscus moscheutos* 'Extrmag'.

Parentage:

*Female, or seed, parent*.—Proprietary selection of *Hibiscus moscheutos* identified as code number CB11023, not patented.

*Male or pollen parent*.—Proprietary selection of *Hibiscus moscheutos* identified as code number CB11046, not patented.

Propagation:

*Type*.—By vegetative cuttings.

*Time to initiate roots, summer*.—About seven days at temperatures about 22° C.

*Time to initiate roots, winter*.—About ten days at temperatures about 19° C.

*Time to produce a rooted young plant, summer*.—About three weeks at temperatures about 21° C.

*Time to produce a rooted young plant, winter*.—About four weeks at temperatures about 18° C.

*Root description*.—Medium in thickness, fibrous; white to light brown in color.

*Rooting habit*.—Freely branching; dense.

Plant description:

*Plant form and growth habit*.—Upright and somewhat outwardly spreading plant form, broad inverted triangular plant form; moderately vigorous growth habit.

*Branching habit*.—Moderate branching habit, usually about nine lateral branches develop; pinching enhances lateral branch development.

*Plant height*.—About 45.5 cm.

*Plant diameter* (*area of spread*): About 57 cm.

Lateral branch description:

*Length*.—About 37.5 cm.

*Diameter*.—About 7 mm.

*Internode length*.—About 2.4 cm.

*Strength*.—Moderately strong.

*Texture*.—Smooth, glabrous.

*Aspect*.—Erect to about 35° from vertical.

*Color*.—Close to 178B; towards the base and lower surface, close to 145A.

Leaf description:

*Arrangement*.—Alternate, single.

*Length*.—About 11.3 cm.

*Width*.—About 8 cm.

*Shape*.—Ovate.

*Apex*.—Apiculate.

*Base*.—Cordate.

*Margin*.—Crenate to bluntly serrate.

*Texture, upper and lower surfaces*.—Smooth, glabrous.

*Venation pattern*.—Pinnate.

*Color*.—Developing leaves, upper surface: Close to N137C. Developing leaves, lower surface: Close to 137B to 137C. Fully expanded leaves, upper surface: Between 137A and N147B; venation, close to 144A, towards the base, tinged with close to 178A. Fully expanded leaves, lower surface: Between 146B and 147B; venation, close to 144B.

*Petioles*.—Length: About 7.1 cm. Diameter: About 3 mm. Texture, upper and lower surfaces: Smooth, glabrous. Color, upper surface: Close to 166B. Color, lower surface: Close to 144C.

Flower description:

*Flower arrangement*.—Large rotate flowers arranged singly at terminal leaf axils; freely flowering habit with about 55 flowers developing per plant; flowers face mostly outwardly to slightly upright.

*Fragrance*.—None detected.

*Flower longevity*.—Good flower longevity, flowers last for about four days; flowers not persistent.

*Natural flowering season*.—Plants flower from late summer into the autumn in The Netherlands; plants begin flowering about nine weeks after planting.

*Flower diameter*.—About 13.5 cm.

*Flower length* (*height*).—About 6.7 cm.

*Flower buds*.—Rate of opening: Flowers buds open in about four days. Length: About 4.4 cm. Diameter: About 2.5 cm. Shape: Ovate. Color: Between 143C and 144A; towards the apex, close to 59A to 59B.

*Petals*.—Arrangement: Corolla consists of five petals in a single whorl; petals slightly imbricate. Length: About 7 cm. Width: About 6.5 cm. Shape: Broadly obovate. Apex: Rounded. Base: Attenuate. Margin: Entire. Texture, upper and lower surfaces: Smooth, glabrous. Color: When opening, upper surface: Between 53C and 60A; towards the base, close to 53A; venation, close to 53A. When opening, lower surface: Between 53C and 60A; venation, close to 53A. Fully opened, upper surface: Close to 61B; towards the base, close to 53A; venation, close to 53A. Fully opened, lower surface: Close to 61B; venation, close to 53A.

*Sepals*.—Appearance: Five sepals fused into a tubular star-shaped calyx. Length: About 2.2 cm. Width: About 1.3 cm. Shape: Ovate. Apex: Acute. Margin: Entire. Texture, upper and lower surfaces: Smooth, glabrous. Color: When opening, upper surface: Close to 144B to 144C. When opening, lower surface: Between 143C and 144A. Fully opened, upper surface: Close to 145A. Fully opened, lower surface: Between 143B and 144A.

*Bracts*.—Quantity per flower: Twelve in a single whorl. Length: About 1.5 cm. Width: About 2 mm. Shape: Lanceolate. Apex: Acute. Texture, upper and lower surfaces: Smooth, glabrous. Color, upper surface: Close to 144A. Color, lower surface: Close to 143A.

*Peduncles*.—Length: About 2.5 cm. Diameter: About 2 mm. Angle: About 30° from the lateral branch axis. Strength: Moderately strong. Texture: Smooth, glabrous. Color, upper surface: Close to 175A to 175B. Color, lower surface: Close to 146A to 146B.

*Reproductive organs*.—Androecium: Stamen number: Numerous, about 120. Filament length: About 4 mm. Filament color: Between 63A and 62B. Anther shape: Orbicular. Anther length: About 2 mm. Anther color: Close to 182B to 182C. Amount of pollen: Moderate. Pollen color: Close to 199D. Gynoecium: Pistil length: About 4.4 cm. Style length: About 4.2 cm. Style color: Between 63A and 62B. Stigma appearance: Five-parted, club-shaped. Stigma color: Close to 53A. Ovary color: Close to 150C.

*Seeds and fruits*.—Seed and fruit development have not been observed on plants of the new *Hibiscus*.

Temperature tolerance: Plants of the new *Hibiscus* have been observed to tolerate high temperatures of about 35° C. and to be hardy to USDA Hardiness Zone 6.

Pathogen & pest resistance: Plants of the new *Hibiscus* have not been observed to be resistant to pathogens and pests common to *Hibiscus*.

It is claimed:

1. A new and distinct *Hibiscus* plant named 'Extrmag' as illustrated and described.

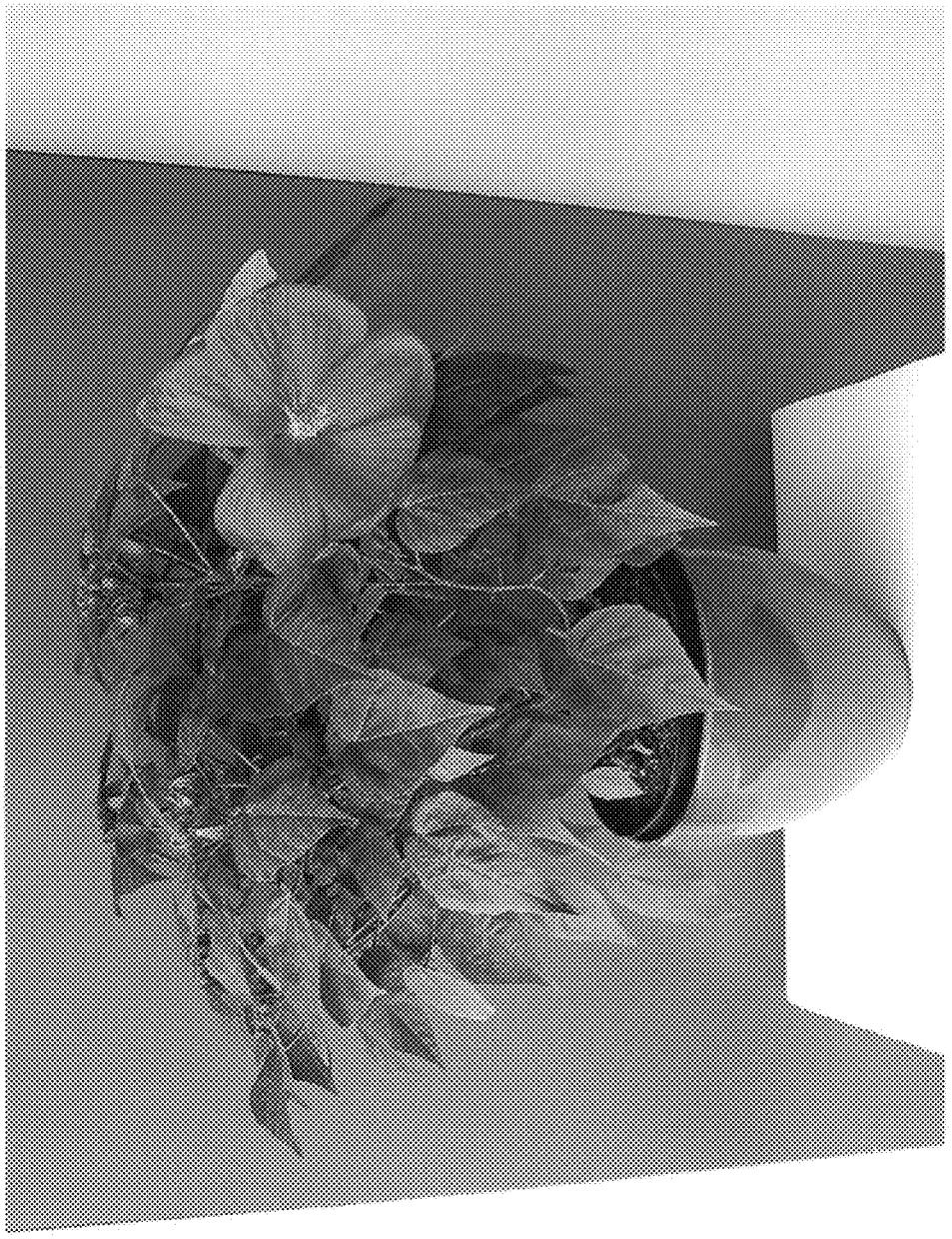

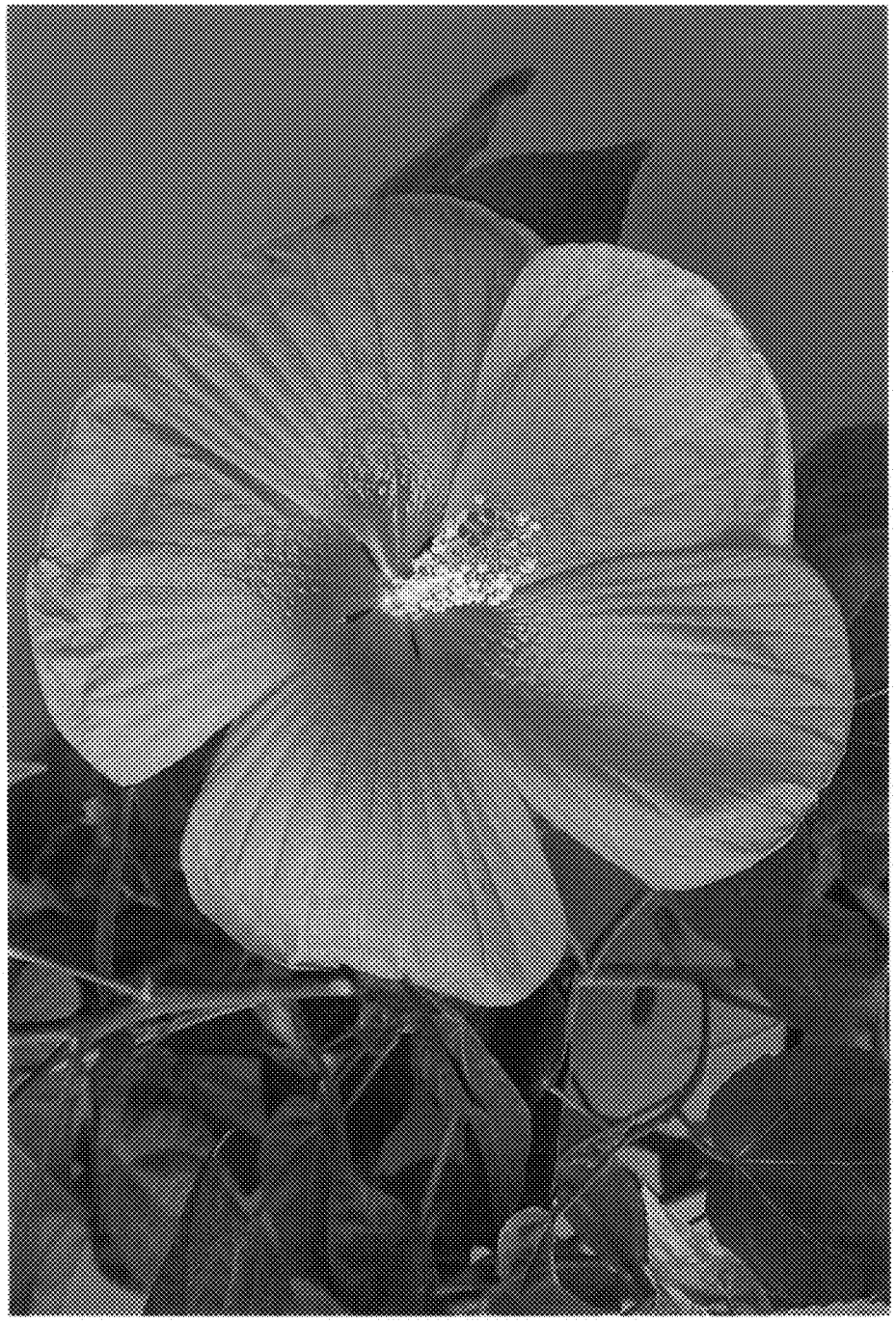

* * * * *